United States Patent [19]

Freidinger et al.

[11] Patent Number: 5,166,151
[45] Date of Patent: Nov. 24, 1992

[54] 2-BENZAZEPINES WITH 5- AND 6-MEMBERED HETEROCYCLIC RINGS, COMPOSITIONS AND MEDICAL METHODS OF USE THEREOF

[75] Inventors: Roger M. Freidinger, Hatfield; Ben E. Evans, Lansdale; Mark G. Bock, Hatfield, all of Pa.

[73] Assignee: Merck & Co., Inc., Rahway, N.J.

[21] Appl. No.: 668,353

[22] Filed: Mar. 11, 1991

Related U.S. Application Data

[63] Continuation of Ser. No. 353,224, May 15, 1989, abandoned, which is a continuation of Ser. No. 175,641, Mar. 25, 1988, abandoned.

[51] Int. Cl.$^5$ .................. C07D 471/04; A61K 31/44; A61K 31/55
[52] U.S. Cl. .................. 514/215; 514/217; 540/578
[58] Field of Search .............. 548/578; 544/216, 217

[56] References Cited

U.S. PATENT DOCUMENTS

| 4,269,774 | 5/1981 | Fryev et al. | 540/578 |
| 4,379,765 | 4/1983 | Field et al. | 540/578 |
| 4,481,142 | 11/1984 | Fryer et al. | 540/578 |
| 4,548,750 | 10/1985 | Fryer et al. | 540/578 |

Primary Examiner—David B. Springer
Attorney, Agent, or Firm—Mark R. Daniel; Joseph F. DiPrima

[57] ABSTRACT

Aromatic 2-benzazepines with fused 5- or 6-membered heterocyclic rings which are antagonists of cholecystokinins and/or gastrin, and are useful in the treatment or prevention of CCK-related and/or gastrin-related disorders of the gastrointestinal, central nervous and appetite regulatory systems; compositions comprising these compounds; and methods of treatment of mammals or of increasing food intake of animals employing these compounds.

16 Claims, No Drawings

2-BENZAZEPINES WITH 5- AND 6-MEMBERED HETEROCYCLIC RINGS, COMPOSITIONS AND MEDICAL METHODS OF USE THEREOF

This is a continuation of application Ser. No. 07/353,224, filed May 15, 1989, which is a continuation of Ser. No. 07/175,641, filed Mar. 28, 1988 both abandoned.

BACKGROUND OF THE INVENTION

Cholecystokinins (CCK) and gastrin are structurally-related neuropeptides which exist in gastrointestinal tissue and in the central nervous system (see, V. Mutt, *Gastrointestinal Hormones*, G. B. J. Glass, Ed., Raven Press, N.Y., p. 169 and G. Nisson, ibid. p. 127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (a naturally-occurring neuropeptide, also, and the minimum fully active sequence), and 39- and 12-amino acid forms, while gastrin occurs in 34-, 17- and 14-amino acid forms, with the minimum active sequence being the C-terminal pentapeptide, Gly-Trp-Met-Asp-Phe-NH$_2$, which is the common structural element shared by both CCK and gastrin.

CCK's are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly co-exist with dopamine in certain mid-brain neurons and thus may also play a role in the functioning of dopaminergic systems in the brain, in addition to serving as neurotransmitters in their own right (see: A. J. Prange et al., "Peptides in the Central Nervous System", *Ann. Repts. Med. Chem.* 17, 31, 33 [1982] and references cited therein; J. A. Williams, *Biomed. Res.* 3 107 [1982]); and J. E. Morley, *Life Sci.* 30, 479, [1982]).

The primary role of gastrin, on the other hand, appears to be stimulation of the secretion of water and electrolytes from the stomach, and, as such, it is involved in control of gastric acid and pepsin secretion. Other physiological effects of gastrin then include increased mucosal blood flow and increased antral motility, with rat studies having shown that gastrin has a positive trophic effect on the gastric mucosa, as evidenced by increased DNA, RNA and protein synthesis.

Antagonists to CCK and to gastrin have been useful for preventing and treating CCK-related and/or gastrin-related disorders of the gastrointestinal (GI) and central nervous (CNS) systems of animals, especially of humans. Just as there is some overlap in the biological activities of CCK and gastrin, antagonists also tend to have affinity for both receptors. In a practical sense, however, there is enough selectivity to the different receptors that greater activity against specific CCK- or gastrin-related disorders can often also be identified.

Selective CCK antagonists are themselves useful in treating CCK-related disorders of the appetite regulatory systems of animals as well as in potentiating and prolonging opiate-mediated analgesia, thus having utility in the treatment of pain [see P. L. Faris et al., Science 226, 1215 (1984)], while selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value.

Also, since CCK and gastrin also have trophic effects on certain tumors [K. Okyama, *Hokkaido J. Med. Sci.*, 60, 206–216 (1985)], antagonists of CCK and gastrin are useful in treating these tumors [see, R. D. Beauchamp et al., *Ann. Surg.*, 202,303 (1985)].

Four distinct chemical classes of CCK-receptor antagonists have been reported. The first class comprises derivatives of cyclic nucleotides, of which dibutyryl cyclic GMP has been shown to be the most potent by detailed structure-function studies (see, N. Barlos et al., *Am. J. Physiol*, 242, G 161 (1982) and P. Robberecht et al., *Mol., Pharmacol.*, 17, 268 (1980)).

The second class comprises peptide antagonists which are C-terminal fragments and analogs of CCK, of which both shorter (Boc-Met-Asp-Phe-NH$_2$, Met-Asp-Phe-NH$_2$), and longer (Cbz-Tyr(SO$_3$H)-Met-Gly-Trp-Met-Asp-NH$_2$) C-terminal fragments of CCK can function as CCK antagonists, according to recent structure-function studies (see, R. T. Jensen et al., *Biochem. Biophys. Acta.*, 757, 250 (1983), and M. Spanarkel et al., *J. Biol. Chem.*, 258, 6746 (1983)). The latter compound was recently reported to be a partial agonist [see, J. M. Howard et al., *Gastroenterology* 86(5) Part 2, 1118 (1984)].

Then, the third class of CCK-receptor antagonists comprises the amino acid derivatives: proglumide, a derivative of glutaramic acid, and the N-acyl tryptophans including para-chlorobenzoyl-L-tryptophan (benzotript), [see, W. F. Hahne et al., *Proc. Natl. Acad. Sci. U.S.A.*, 78, 6304 (1981), R. T. Jensen et al., *Biochem. Biophys. Acta.*, 761, 269 (1983)]. All of these compounds, however, are relatively weak antagonists of CCK (IC$_{50}$: generally 10$^{-4}$M[although more potent analogs of proglumide have been recently reported in F. Makovec et al., *Arzneim-Forsch Drug Res.*, 35 (II), 1048 (1985) and in German Patent Application DE 3522506A1], but down to 10$^{-6}$M in the case of peptides), and the peptide CCK-antagonists have substantial stability and absorption problems.

In addition, a fourth class consists of improved CCK-antagonists comprising a nonpeptide of novel structure from fermentation sources [R. S. L. Chang et al., *Science*, 230, 177–179 (1985)] and 3-substituted benzodiazepines based on this structure [published European Patent Applications 167 919, 167 920 and 169 392, B. E. Evans et al, *Proc. Natl. Acad. Sci. U.S.A.*, 83, p. 4918–4922 (1986) and R. S. L. Chang et al, ibid, p. 4923–4926] have also been reported.

No really effective receptor antagonists of the in vivo effects of gastrin have been reported (J. S. Morley, *Gut Pept. Ulcer Proc., Hiroshima Symp.* 2nd, 1983, p. 1), and very weak in vitro antagonists, such as proglumide and certain peptides have been described [(J. Martinez, *J. Med. Chem.* 27. 1597 (1984)]. Recently, however, pseudopeptide analogs of tetragastrin have been reported to be more effective gastrin antagonists than previous agents [J. Martinez et al., *J. Med. Chem.*, 28, 1874–1879 (1985)].

The benzodiazepine (BZD) structure class, which has been widely exploited as therapeutic agents, especially as central nervous system (CNS) drugs, such as anxyolitics, and which exhibits strong binding to "benzodiazepine receptors" in vitro, has not in the past been reported to bind to CCK or gastrin receptors. The same situation exists for the structurally-related benzazepines. Benzodiazepines have been shown to antagonize CCK-induced activation of rat hippocampal neurones but this effect is mediated by the benzodiazepine receptor, not the CCK receptor [see J. Bradwejn et al., *Nature*, 312, 363 (1984)]. Of these reported BZD's, additionally, the large majority do not contain substituents attached to the 3-position of the seven membered ring, as it is well known in the art that 3-substituents result in decreasing anxiolitic activity, especially as these substituents increase in size. Further, it has been demonstrated that in the case of the 3-substituted benzodiazepines that have been reported, the preferred stereochemistry at position 3 for CNS activity is S, which would correspond to an L-amino acid, such as L-tryptophan.

It was, therefore, an object of this invention to identify substances which more effectively antagonize the function of cholecystokinins and/or gastrin in disease states in mammals, especially in humans. It was another object of this invention to prepare novel compounds which more selectively inhibit cholecystokinins or inhibit gastrin. It was still another object of this invention to develop a method of antagonizing the functions of cholecystokinin and/or gastrin in disease states in mammals. It is also an object of this invention to develop a method of preventing or treating disorders of the gastrointestinal, central nervous and appetite regulatory systems of mammals, especially of humans, or of increasing food intake of animals.

SUMMARY OF THE INVENTION

The present invention is directed to aromatic 2-benzazepines with fused 5- or 6-membered heterocyclic rings of Formula I which are antagonists of cholecystokinins (CCK) and/or gastrin, and are useful in the treatment and prevention of CCK-related and/or gastrin-related disorders of the gastro-intestinal, central nervous and appetite regulatory systems of mammals, especially of humans, including irritable bowel syndrome, ulcers, excess pancreatic or gastric secretion, acute pancreatitis, motility disorders, neuroleptic disorders, tardive dyskinesia, Parkinson's disease, psychosis, Gilles de la Tourette Syndrome, disorders of the appetite regulatory system, Zollinger-Ellison syndrome, antral G cell hyperplasia, pain (by the potentiation of opioid analgesics), and malignancies of the lower esophagus, stomach, intestines, and colon. As antagonists of CCK, they may also be used to increase food intake in animals.

DETAILED DESCRIPTION OF THE INVENTION

The compounds of this invention are those of Formula I:

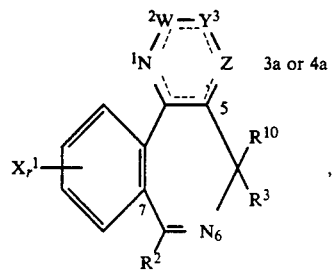

wherein
$R^1$ is H, $C_1$-$C_4$-alkyl cyclo-$C_3$-$C_7$-alkyl,

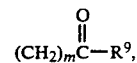

$NR^4R^5$, $C_1$-$C_4$-alkoxy, thio-$C_1$-$C_4$-alkoxy, OH, or SH;

$R^2$ is H, $C_1$-$C_4$-alkyl, mono- or disubstituted or unsubstituted phenyl (wherein the substitutent(s) is/are independently selected from the group consisting of halo, $C_1$-$C_4$-alkyl, $C_1$-$C_4$-alkoxy, $C_1$-$C_4$-alkylthio, carboxyl, carboxy-$C_1$-$C_4$-alkyl, nitro, —$CF_3$,

and hydroxy), 2-, 3- or 4-pyridyl or —$(CH_2)_mCOOR^6$;
$R^3$ is —$(CH_2)_nR^7$,

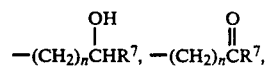

—$(CH_2)_nNR^{18}(CH_2)_qR^7$,

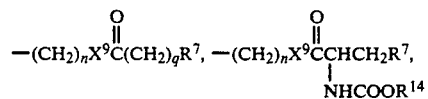

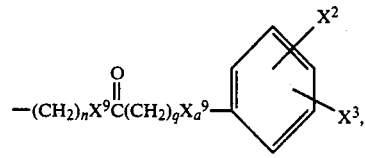

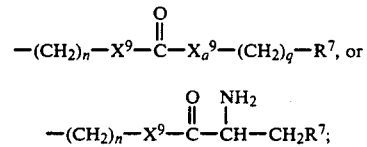

$R^4$ and $R^5$ are independently H, $C_1$-$C_4$-alkyl, or cyclo-$C_3$-$C_7$-alkyl, or are connected to form a hetero ring of the structure

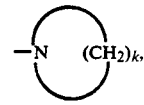

wherein k is 2 to 6;
$R^6$ is H, $C_1$-$C_4$-alkyl, cyclo-$C_3$-$C_7$-alkyl, unsubstituted or mono- or disubstituted phenyl (wherein the substituent(s) is/are independently selected from the group consisting of halo, $C_1$-$C_4$-alkyl, $C_1$-$C_4$-alkoxy, nitro, and $CF_3$), or unsubstituted or mono- or disubstituted phenyl-$C_1$-$C_4$-alkyl (wherein the substituent(s) is/are independently selected from the group consisting of halo, $C_1$-$C_4$-alkyl, $C_1$-$C_4$-alkoxy, nitro, and $CF_3$);

$R^7$ is α- or β-naphthyl, unsubstituted or mono- or disubstituted phenyl (wherein the substituent(s) is/are independently selected from the group consisting of halo, —$NO_2$, —OH, —$NR^4R^5$, $C_1$-$C_4$-alkyl, cyano, phenyl, trifluoromethyl, acetylamino, acetyloxy, $C_1$-$C_4$-alkylthio, $SCF_3$, $C \equiv CH$, $CH_2SCF_3$, S-phenyl, or $C_1$-$C_4$-alkoxy),

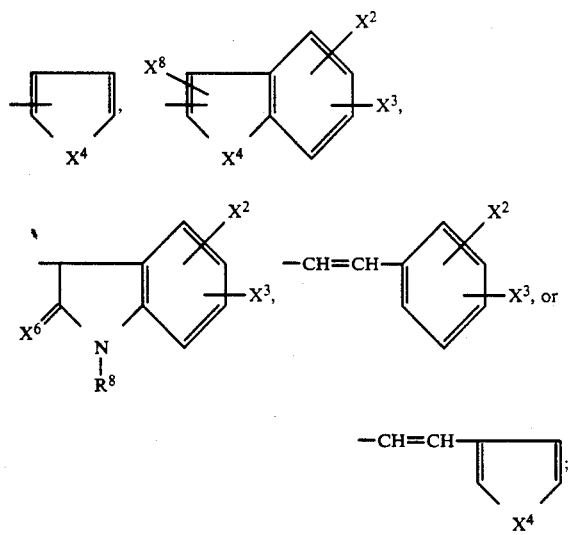

$R^8$ is H, $C_1$-$C_4$-alkyl, cyclo-$C_3$-$C_7$-alkyl, —$(CH_2)_n$-cyclo-$C_3$-$C_7$-alkyl,

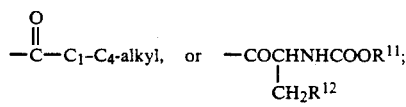

$R^9$ is OH, $OR^{11}$ or

$R^{10}$ is H, —OH, or —$CH_3$;
$R^{11}$ and $R^{12}$ are independently $C_1$-$C_4$-alkyl or cyclo-$C_3$-$C_7$-alkyl;
$R^{13}$ is

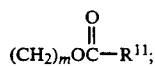

$R^{14}$ is $C_1$-$C_4$-alkyl or phenyl-$C_1$-$C_4$-alkyl;
$R^{18}$ is H, $C_1$-$C_4$-alkyl, formyl, acetyl, propionyl or butyryl;
m is 1 to 4;
n is 0 to 4;
q is 0 to 4;
r is 1 or 2;
$X^1$ is H, —$NO_2$, $CF_3$, CN, OH, $C_1$-$C_4$-alkyl, halo, $C_1$-$C_4$-alkylthio, $C_1$-$C_4$-alkoxy, —$(CH_2)_nCOOR^6$, —$NR^4R^5$, or

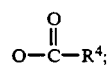

$X^2$ and $X^3$ are independently H, —OH, —$NO_2$, halo, $C_1$-$C_4$-alkylthio, $C_1$-$C_4$-alkyl, $C_1$-$C_4$-alkoxy or

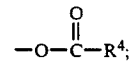

$X^4$ is S, O, $CH_2$, or $NR^8$;
$X^6$ is O or HH;
$X^8$ is H or $C_1$-$C_4$-alkyl;
$X^9$ and $X_a^9$ are independently $NR^{18}$ or O;
W is $CR^1$, N or NH;
Y is N, S, or O;
Z is C—H or absent; and
----- is a saturated (single) or unsaturated (double) bond;
and the pharmaceutically-acceptable salts thereof.

The stereochemistry of the compounds may be D, L or DL.

As used herein, the definition of each expression, e.g., m, n, p, loweralkyl, etc., when it occurs more than once in any structure, is intended to be independent of its definition elsewhere in the same structure.

However, in the compounds of Formula I, the preferred stereochemistry for CCK-antagonism relates to D-tryptophan, where $C^{3a}$ and $N^5$ ($C^{4a}$ and $N^6$ for pyrimido analogs) of Formula I correspond to the carbonyl carbon and α-amino nitrogen of D-tryptophan respectively, and $R^3$ occupies the position of the indolylmethyl side chain. Then, in the compounds of Formula I, the preferred stereochemistry for gastrin antagonism may be either D or L depending on the nature of $R^3$. For example, when $R^3$ is $(CH_2)_nR^7$ or

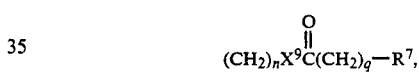

the preferred stereochemistry corresponds to D-tryptophan, as above, and when $R^3$ is

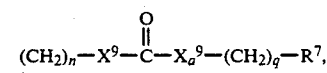

the preferred stereochemistry corresponds to L-tryptophan.

As used herein, halo is F, Cl, Br, or I and $C_1$-$C_4$-alkyl groups are either straight or branched-chain alkyl and include methyl, ethyl, propyl, isopropyl, butyl, isobutyl, and t-butyl.

Preferred compounds according to the present invention are those wherein $R^1$ is H or methyl, $R^2$ is phenyl or o-F-phenyl, $R^3$ is

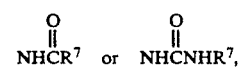

$R^7$ is

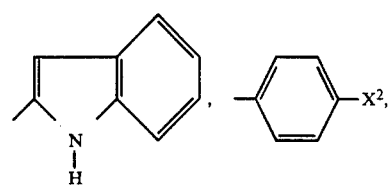

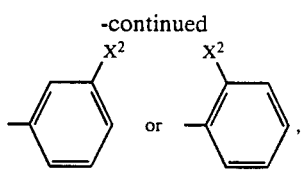 or 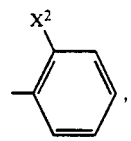, $X^1$ and $X^2$ are independently H, —NO$_2$, halo, methyl, or methoxy, and either: W is CR$^1$, Y is N and Z is CH; or W is CR$^1$, Y is S and Z is absent; or W is CR$^1$, Y is O and Z is absent; or W is NH, Y is N and Z is absent. For preventing gastrin-related problems, preferred compounds are those wherein R$^3$ is

R$^7$ is

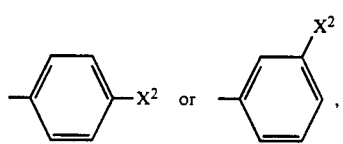

and the stereochemistry corresponds to L-tryptophan. For preventing and treating CCK-related problems, preferred compounds are those wherein R$^3$ is

R$^7$ is

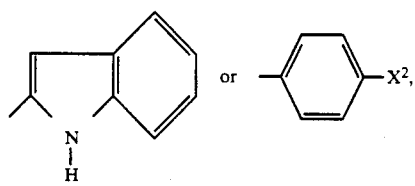

$X^2$ is halo and wherein R$^3$ is

R$^7$ is and the stereochemistry corresponds to D-tryptophan. Such particularly preferred compounds include, for CCK-antagonism:

5(S)-5-(2-indolecarbonylamino)-7-phenyl-5H-pyrimido-[5,4-d][2]benzazepine;
4(S)-4-(4-chlorophenylcarbonylamino)-2-methyl-6-phenyl-4H-thiazolo-[5,4-d][2]benzazepine;
4(S)-4-(2-indolecarbonylamino)-6-phenyl-4H-oxazolo-[5,4-d][2]benzazepine; and
4(S)-4-(2-indolecarbonylamino)-6-phenyl-2H,4H-[1,2,3]-triazolo-[5,4-d][2]benzazepine:

and for gastrin antagonism:

5(R)-5-(3-methoxyphenylaminocarbonylamino)-7-phenyl-5H-pyrimido[5,4-d][2]benzazepine;
4(R)-4-(3-methylphenylaminocarbonylamino)-2-methyl-6-phenyl-4H-thiazolo-[5,4-d][2]benzazepine;
4(R)-4-(3-chlorophenylaminocarbonylamino)-6-phenyl-4H-oxazolo-[5,4-d][2]benzazepine; and
4(R)-4-(3-methoxyphenylaminocarbonylamino)-6-phenyl-2H,4H -[1,2,3]triazolo-[5,4-d][2]benzazepine.

The pharmaceutically-acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, phosphoric, nitric and the like; and the salts prepared from organic acids such as acetic, propionic, succinic, glycolic, stearic, lactic, malic, tartaric, citric, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, isethionic, and the like.

The compounds of Formula I are particularly distinguished from benzazepines of the prior art by the presence of 3-substituents. These Formula I compounds bind strongly to CCK-receptors, but only weakly to benzodiazepine-receptors, especially with the increasing size of the 3-substituent.

Compounds according to Formula (I) may be prepared according to Scheme I through VIII as follows:

SCHEME I

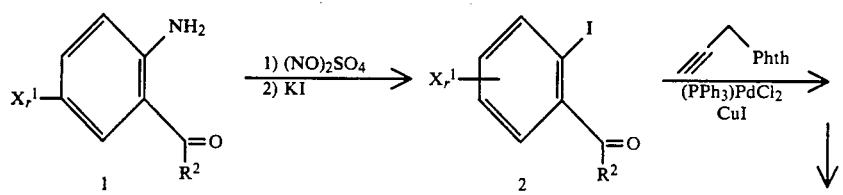

-continued
SCHEME I
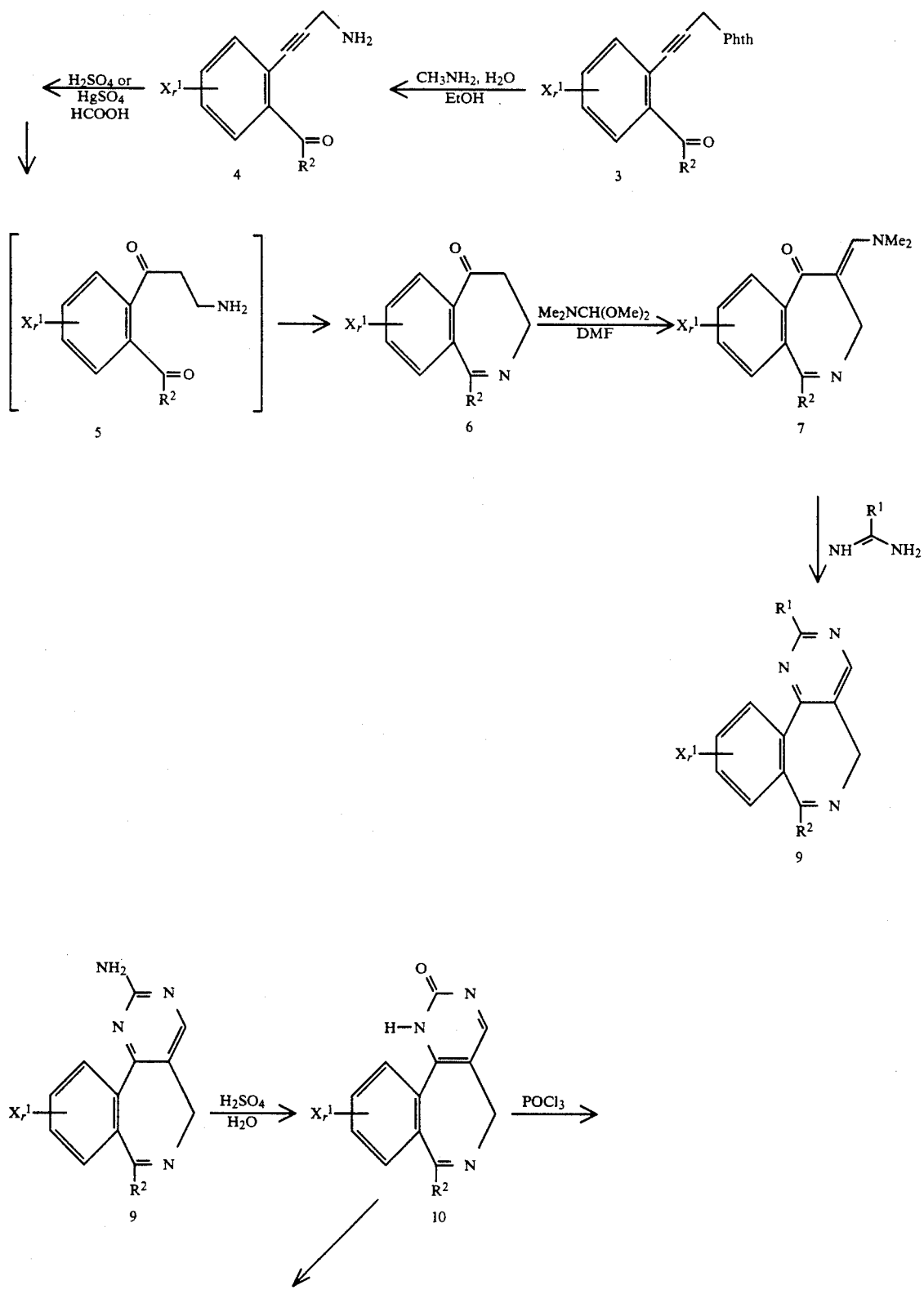

-continued
SCHEME I
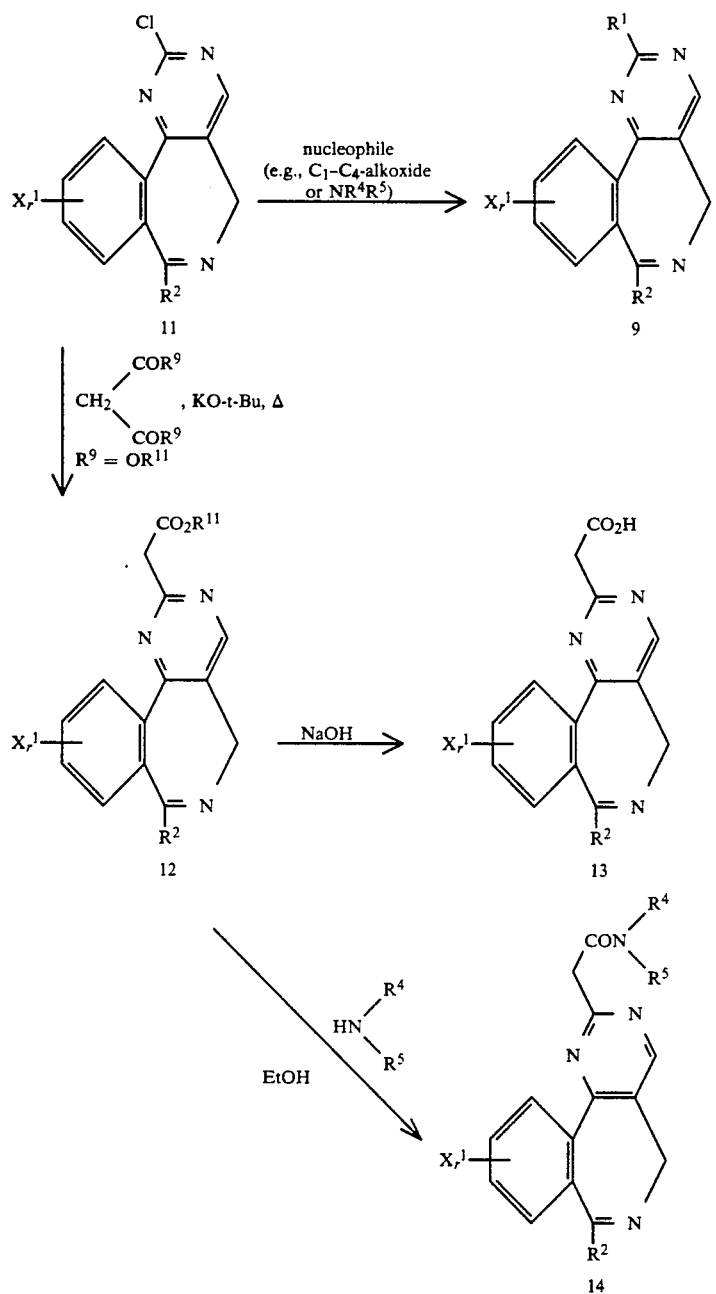
*Phth = phthalimido.
SCHEME II
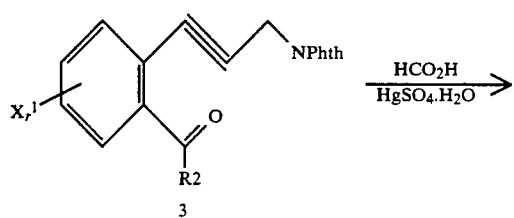

SCHEME II
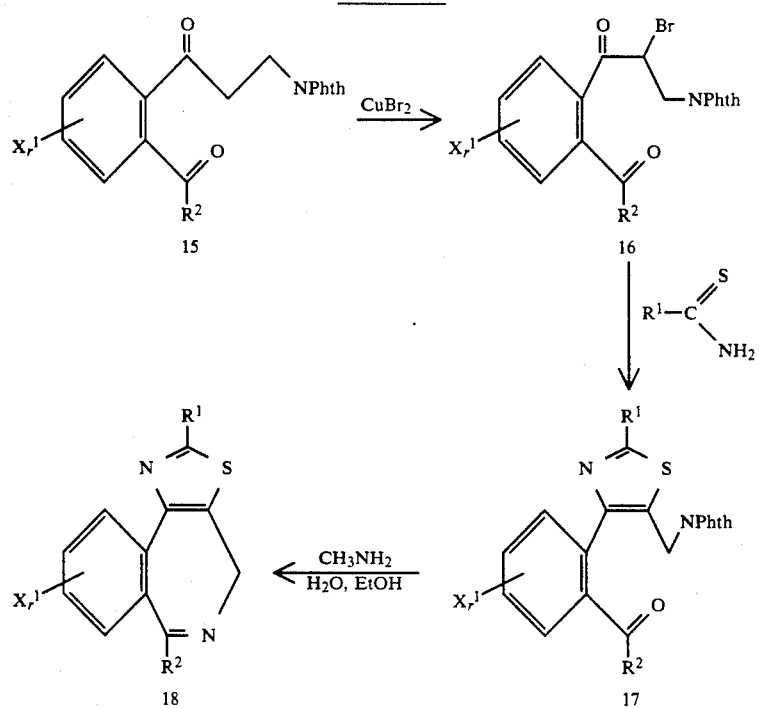
SCHEME III
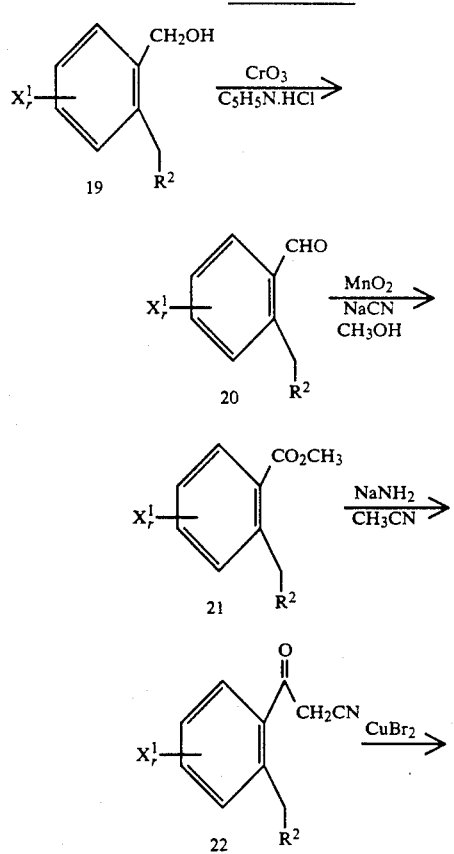
-continued
SCHEME III
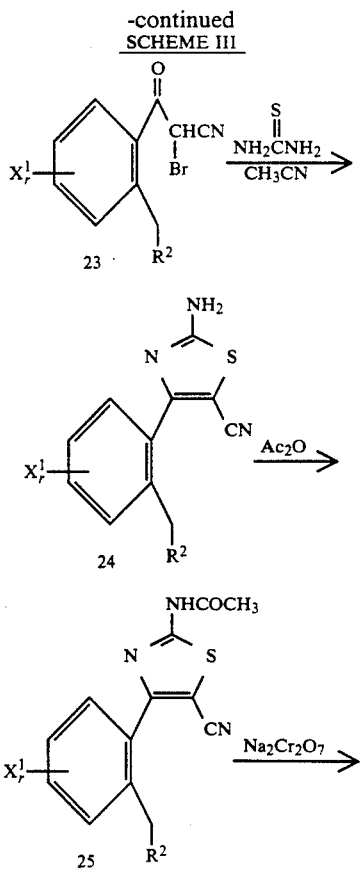

5,166,151
-continued
SCHEME III
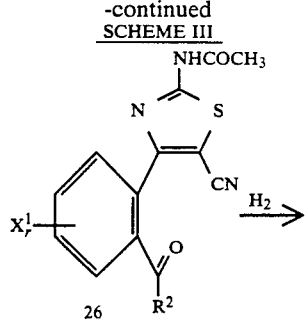
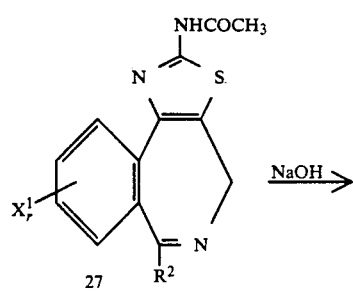
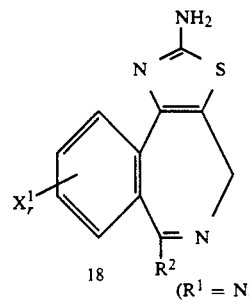
(R¹ = NH₂)
SCHEME IV
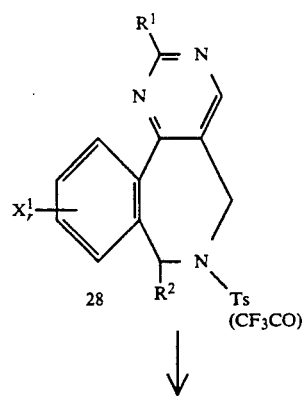
-continued
SCHEME IV
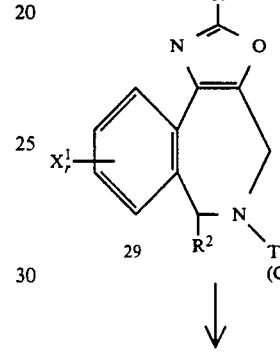
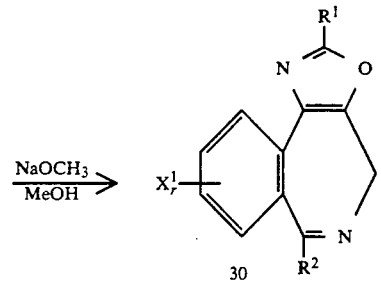
SCHEME
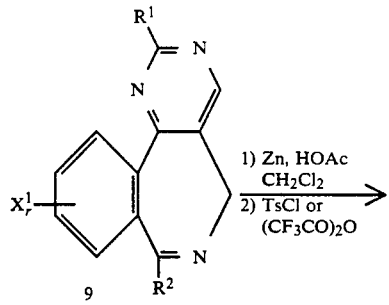
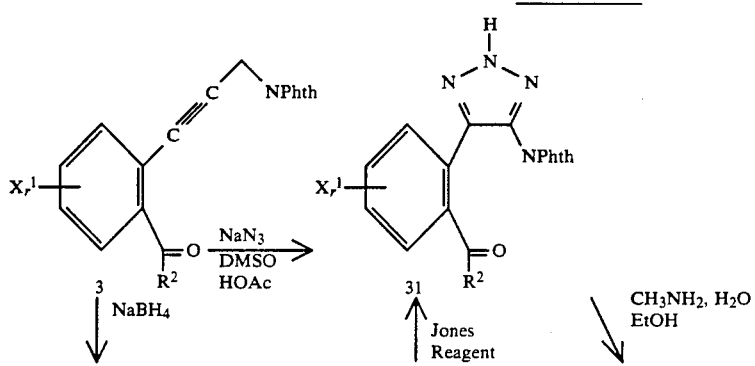
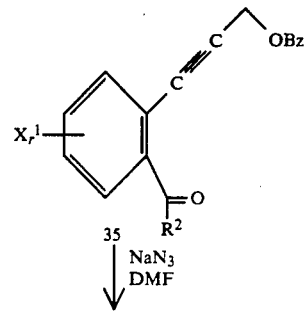

-continued
SCHEME
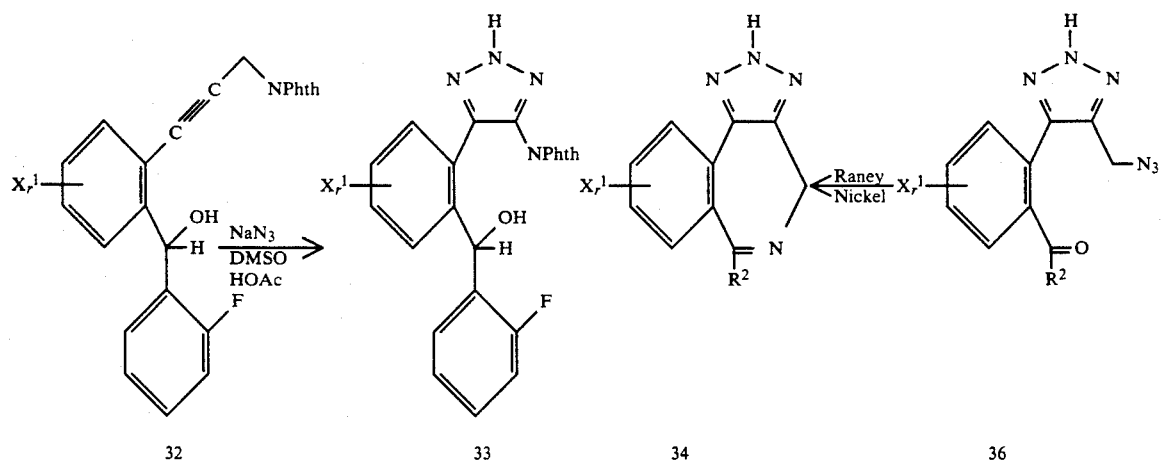
REACTION SCHEME VI
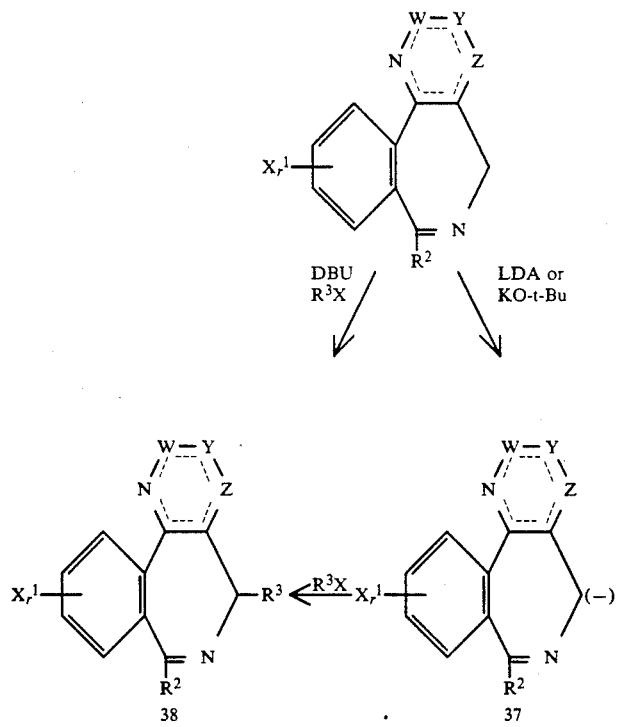
(Where in $R^3$, n is at least 1, when the attachment atom to $R^7$ is C, and otherwise, n is at least 2)
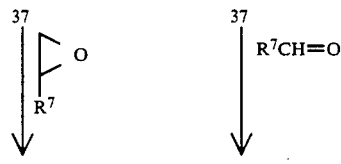

-continued
REACTION SCHEME VI
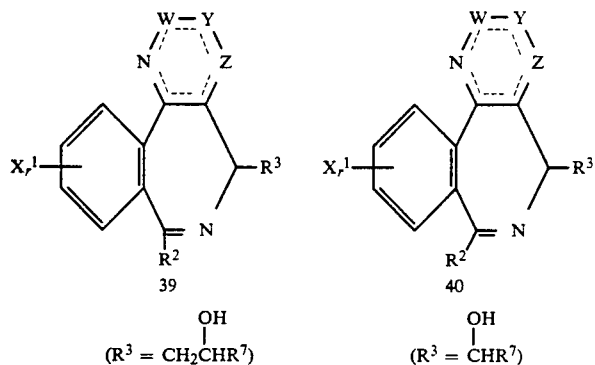
REACTION SCHEME VII
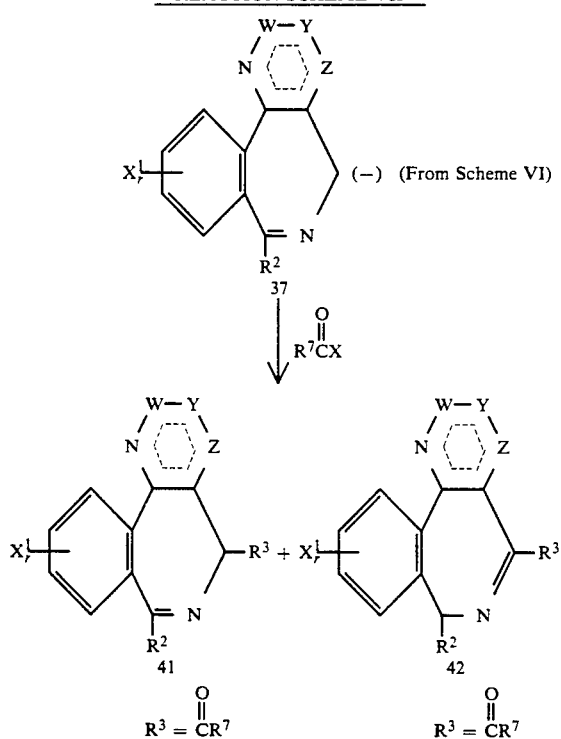
-continued
REACTION SCHEME VII
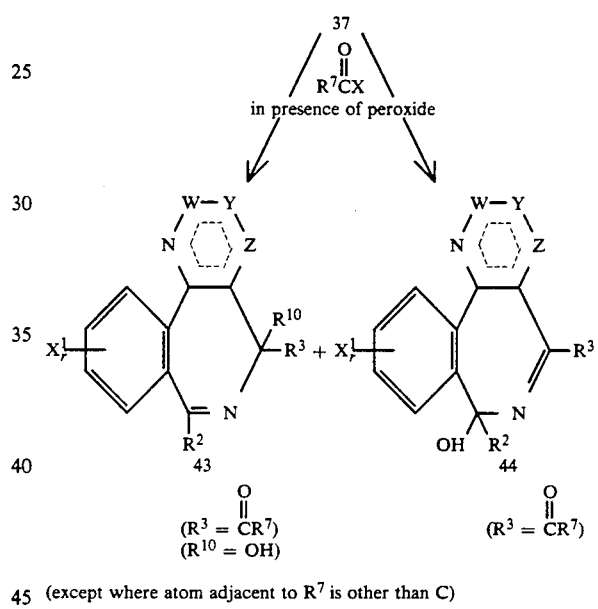
(except where atom adjacent to $R^7$ is other than C)
REACTION SCHEME VIII
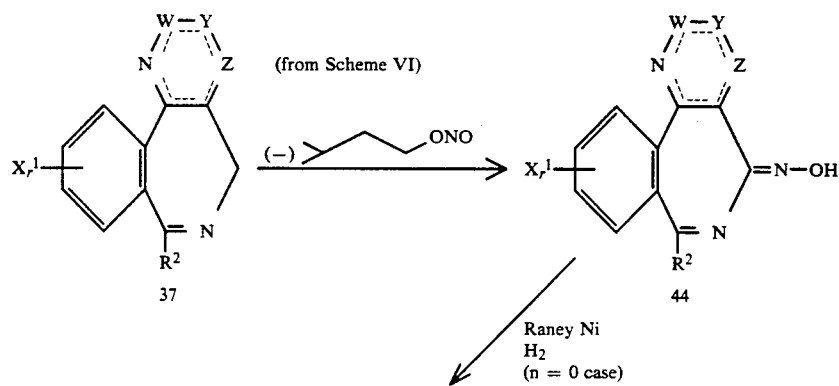

REACTION SCHEME VIII
-continued

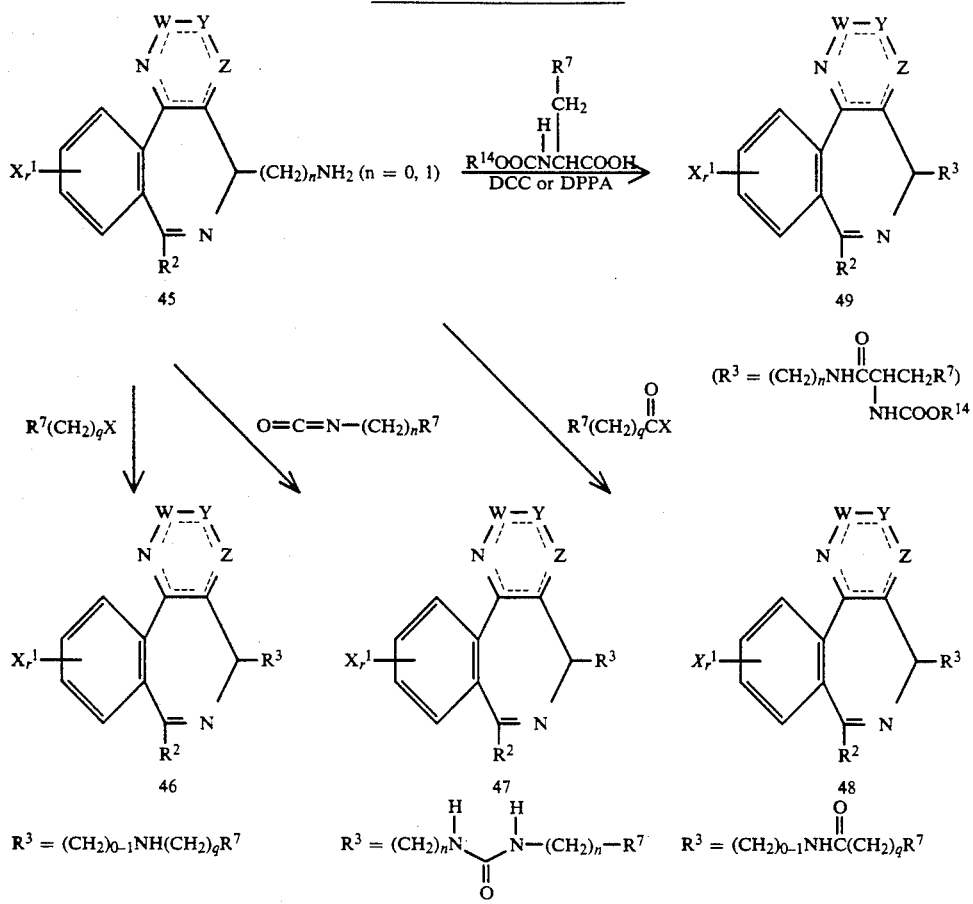

Referring to Reaction Scheme I, the iodobenzophenone 2 required for the palladium catalyzed coupling reaction between the aryl iodide and monosubstituted acetylene, is readily prepared by diazotization of the corresponding o-aminobenzophenone 1 with nitrosyl sulfate followed by treatment of the diazonium salt with aqueous potassium iodide. The coupling of 2 with propargylphthalimide in the presence of dichlorobis(triphenylphosphine)palladium (II) and cuprous iodide in a mixture of diethylamine and methylene chloride yields the acetylenic benzophenone 3. Removal of the phthaloyl protecting group from 3 with 40% aqueous methylamine in ethanol gives the amine 4, in approximately quantitative yield, which contains the atoms necessary for construction of the benzazepine ring. Hydration of the acetylene in 4 with either cold concentrated sulfuric acid or with mercuric sulfate in formic acid gives, after basification of the reaction medium, the 2-benzazepin-5-one 6, presumably via the amino ketone 5.

Treatment of 6 with dimethylformamide dimethyl acetal in DMF between room temperature and 80° C. gives in high yield the (dimethylamino)methylene ketone 7. The addition of reagents, exemplified by acetamidine, isobutyramidine, thiourea, and guanidine, to 7 in the presence of sodium methoxide leads to the corresponding 2-substituted pyrimidobenzazepines 9.

Continuing with Reaction Scheme I, the 2-amino derivative 9 proves to be a useful compound for preparing pyrimidobenzazepines having substituents in the 2-position that were not readily accessible via 7 and the appropriately-substituted guanidine or amidine. Hydrolysis of 9 with aqueous sulfuric acid gives the pyrimidone 10, which, when treated with phosphorous oxychloride leads to the chloro derivative 11. Displacement of the chloride in 11 with an alkoxide or an amine gives the corresponding alkoxy or amino derivatives 9. In addition, reaction of 11 with sodium malonate esters gives upon workup the esters 12. Hydrolysis of 12 with aqueous sodium hydroxide leads to the acid 13; treatment of 12 with amines yields 14.

The starting materials for the preparation of thiazolo[5,4-d][2] benzazepines are the acetylenic compounds 3. Hydration of 3 with formic acid/water in the presence of mercuric sulfate gives the ketones 15. Bromination of 15 with cupric bromide yields the bromo ketones 16, which condenses readily with thiourea or thioamide derivatives to give the thiazoles 17. Removal of the phthaloyl group by treatment of 17 with methylamine gives the thiazolo[5,4-d][2]benzazepines 18, see Scheme II.

A less efficient synthesis of compound 18 starts with the alcohol 19, and is outlined in Scheme III. Oxidation of 19 with pyridinium chlorochromate gives the aldehyde 20, which is further oxidized by the method of Corey et al., (J. Amer. Chem. Soc., (1968) 90, 5616), and gives the methyl ester 21. Condensation of 21 with the anion of acetonitrile gives the keto nitrile 22. Treatment of 22 with cupric bromide gives the bromo ketone 23, which, without purification, is condensed with thiourea to give the thiazole 24. Treatment of 24 with acetic anhydride gives 25, which is oxidized to the ketone 26. Hydrogenation of 26 with Raney nickel as catalyst gives directly the cyclized 2-benzazepine 27. Basic hydrolysis of 27 gives the amine 18, identical with the product prepared by the method of Scheme II.

Referring to Scheme IV, pyrimidobenzazepine 9 is reduced with zinc in acetic acid and methylene chloride, and the resultant amine is protected as either the p-toluenesulfonate or trifluoroacetate. Oxidation of 28 with meta-chloroperbenzoic acid gives oxazole 29 and some pyrimidine N-oxide. Treatment of 29 with sodium methoxide gives oxazolobenzazepine 30.

The readily-available acetylenic benzophenones 3, whose preparation has been described in Scheme I, provides a convenient starting point for the synthesis of triazolobenzazepine ring systems, as shown in Scheme V. Treatment of 3 with sodium azide in warm dimethyl sulfoxide containing acetic acid results in the formation of the triazoles 31. Removal of the phthaloyl group from 31 with 40% aqueous methylamine in ethanol generates the opened derivatives, which spontaneously ring closes to the desired triazolobenzazepines 34, respectively.

When the benzophenone is substituted in the ortho position with a halogen atom, the sodium azide addition to the acetylene requires the use of at least 1 equiv of acetic acid or a similar proton source. In the absence of acetic acid, the initially formed triazole anion displaces the ortho halogen and results in the formation of 9 triazolodibenzazepine. The use of acetic acid allows protonation of the initially formed anion, and the resulting triazole, a weaker nucleophile, is less likely to displace the halogen. This method works well where the ortho substituent is chlorine. The displacement of fluorine in 31 can not be satisfactorily suppressed with acetic acid; thus, it is necessary to deactivate the carbon atom bearing fluorine by reduction of the carbonyl group to give the benzhydrol 32. Reaction of 32 with sodium azide and acetic acid in dimethyl sulfoxide gives the triazole 33. Oxidation of 33 with Jones reagent gives 31.

An alternate procedure for the synthesis of 34 utilizes the reaction of sodium azide with the benzoate 35. By this method, not only is the triazole ring formed but also azide ion displaces the benzoate group in 35, resulting in the triazolo azide 36. Hydrogenation of 36 with Raney nickel as catalyst gives the amino compound, which cyclizes in situ to the triazolobenzazepine 34.

Referring now to Reaction Scheme VI, the anion 37 is generated from compounds produced in Schemes I–V by the procedure of *J. Org. Chem.*, 46, 3945 (1981) using lithium diisopropylamide (LDA) or using potassium tert-butoxide.

The compound 37 may be variously treated. For example, the hydroxy alkyl derivative 40 is generated by adding an aldehyde to a solution of 37. Treatment of 37 with an epoxide yields the hydroxyethyl derivative 39. By treating 37 with an alkyl halide, the alkyl derivative 38 is produced.

An alternative procedure for obtaining 37 is to treat the compounds from Schemes I–V with an alkyl halide and a strong base such as 1,8-diazabicyclo[5.4.0]undec-7-ene (DBU) and heating.

Reaction Scheme VII describes the formation of $R^3$ = keto compounds of Formula I. These are produced by treating the anion 37 with an acid halide or anhydride. This reaction produces both isomers 41 and 42. When the reaction is run in the presence of peroxide, the hydroxy compounds 43 and 44 are produced.

Reaction Scheme VIII describes the formation of Formula I compounds where $R^3$ is a substituted amino or aminomethyl. The heterocycle fused benzazepines are either known or readily derivable from known compounds. The amino compounds may also be obtained by nitrosation of 37 followed by reduction of the oxime 44 with Raney nickel and hydrogen.

When 45 is treated with an alkyl halide, the N-alkyl derivative 46 is produced. Treatment of 45 with an acid halide or anhydride produces the N-acyl derivative 48. Compound 45 may also be treated with an N-protected α-amino acid and a coupling reagent such as DCC or DPPA (diphenylphosphorylazide) to give the amides of structure 49. Treatment of compound 45 with an isocyanate gives the ureas 47.

The pharmaceutically-acceptable salts of the present invention may be synthesized from the compounds of Formula I which contain an acidic moiety by conventional chemical methods. Generally, the salts are prepared by reacting the free acid with stoichiometric amounts of or with an excess of the desired salt-forming inorganic or organic base in a suitable solvent or in various combinations of solvents.

The pharmaceutically-acceptable salts of the compounds of Formula I include the conventional non-toxic salts of the compounds of Formula I prepared by conventional procedures, such as treating a basic moiety of Formula I with an appropriate amount of an inorganic acid, such as hydrochloric, hydrobromic, sulfuric, phosphoric, nitric and the like or an organic acid, such as acetic, propionic, succinic, glycolic, stearic, lactic, malic, tartaric, citric, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, isethionic, and the like.

Screening of the novel compounds according to the present invention to determine biological activity and obtain an $IC_{50}$ value for them (in order to identify significant CCK-antagonism), may be accomplished using an $^{125}I$-CCK-receptor binding assay and in vitro isolated tissue preparations. To identify significant gastrin antagonism, $^{125}I$-gastrin and $^3H$-pentagastrin binding assays are used. These tests involve the following:

CCK receptor binding (pancreas) method

CCK-8, radiolabeled with $^{125}I$-Bolton Hunter reagent (2000 Ci/mmole), is purchased from New England Nuclear (NEN) and receptor binding is performed according to Innis and Snyder (*Proc. Natl. Acad. Sci.*, 77, 6917–6921, 1980), with minor modifications as described in Chang and Lotti (*Proc. Natl. Acad. Sci. U.S.A.*, 83, 4923–4926, 1986).

The whole pancreas of a male Sprague-Dawley rat (200–350 g), which has been sacrificed by decapitation, is dissected free of fat tissue and homogenized in 20 volumes of ice-cold 50 mM Tris HCl (pH 7.7 at 25° C.) with a Brinkmann Polytron PT-10. The homogenates are centrifuged at 48,000 g for 10 minutes, then the resulting pellets are resuspended in Tris Buffer, centrifuged as above, and resuspended in 200 volumes of binding assay buffer (50 mM Tris HCl, pH 7.7 at 25° C., 5 mM dithiothreitol and 0.1 mM bacitracin).

For the binding assay, 25 μl of buffer (for total binding), or unlabeled CCK-8 sulfate sufficient to give a final concentration of 1 μM of CCK-8 (for nonspecific binding), or the compounds according to the instant invention (for determination of antagonism to $^{125}$I-CCK binding) and 25 μl of $^{125}$I-CCK-8 (30,000–40,000 cpm), are added to 450 μl of the membrane suspensions in duplicate or triplicate test tubes. The reaction mixtures are incubated at 37° C. for 30 minutes and then filtered on glass fiber GF/B filters, which are then rapidly washed with 3×4 ml of ice cold Tris HCl containing 1 mg/ml BSA, and the filters are counted with a Beckman Gamma 5000. For Scatchard analysis to determine the mechanism of inhibition of $^{125}$I-CCK binding by the most potent compounds (*Ann. N.Y. Acad. Sci.* 51, 660, 1949), $^{125}$I-CCK-8 is progressively diluted with increasing concentrations of CCK-8.

CCK receptor binding (brain) method $^{125}$I-CCK-8 binding is performed similarly to the method described by Saito et al., (*J. Neurochem.*, 37, 483–490, 1981), with modifications described by Chang and Lotti (*Proc. Natl. Acad. Sci.*, 4923–4924, 1986).

Male Hartley guinea pigs (300–500 g) are sacrificed by decapitation, and the brains are removed and placed in ice-cold 50 mM Tris HCl (Trizma-7.4) [pH 7.4 at 25° C.]. The cerebral cortex is dissected and used as a receptor source and each gram of fresh guinea pig brain tissue is homogenized in 10 ml of Tris/Trizma buffer with a Brinkmann polytron PT-10. The homogenates are centrifuged at 42,000 g for 15 minutes, then the resulting pellets are resuspended in 200 volumes of binding assay buffer (10 mM N-2-hydroxyethylpiperazine-N'-2-ethanesulfonic acid (HEPES), 5 mM MgCl$_2$, 1 mM ethylene glycol-bis-(β-aminoethylether)-N,N'-tetraacetic acid (EGTA), 0.4% BSA (bovine serum albumin) and 0.25 mg/ml bacitracin, (pH 6.5).

The remainder of the binding assay method is as described for the pancreas method, except that the reaction mixtures are incubated at 25° C. for 2 hours before centrifugation.

Isolated quinea pig gall bladder method

The two halves of the gall bladders, free of adjacent tissue, of male Hartley guinea pigs (400–600 g), which have been sacrificed by decapitation, are suspended under 1 g tension along the axis of the bile duct in 5 ml organ bath, containing a Kreb's bicarbonate solution of 118 mM NaCl, 4.75 mM KCl, 2.54 mM CaCl$_2$, 1.19 mM KH$_2$PO$_4$, 1.2 mM MgSO$_4$, 25 mM NaHCO$_3$ and 11 mM dextrose, which is maintained at 32° C. and bubbled with a mixture of 95% O$_2$ and 5% CO$_2$. The tissues are washed every 10 minutes for one hour to obtain equilibrium prior to the beginning of the study and the isometric contractions of the strips are recorded using Statham (60g:0.12 mm) strain gauges and a Hewlett-Packard 77588 recorder.

CCK-8 is added cumulatively to the baths and EC$_{50}$'s are determined using regression analysis. After washout (every 10 minutes for one hour), the compound to be tested is added at least 5 minutes before the addition of CCK-8 and the EC$_{50}$ of CCK-8 in the presence of compound to be tested is similarly determined.

A shift to the right of the CCK dose response curve without reduction of the maximal centractile response, indicates competitive antagonism of CCK from this method.

Isolated longitudinal muscle of quinea pig ileum

Longitudinal muscle strips with attached nerve plexus are prepared as described in *Brit. J. Pharmac.* 23:356–363, 1964; *J. Physiol.* 194: 13–33, 1969. Male Hartley guinea pigs are decapitated and the ileum removed (10 cm of the terminal ileum is discarded and the adjacent 20 cm piece used) with a 10 cm piece of the ileum being stretched on a glass pipette. Using a cotton applicator to stroke tangentially away from the mesentery attachment at one end, the longitudinal muscle is separated from the underlying circular muscle and the longitudinal muscle is tied to a thread and by gently pulling, stripped away from the entire muscle. A piece of approximately 2 cm is suspended in 5 ml organ bath containing Krebs solution and bubbled with 95% O$_2$ and 5% CO$_2$ at 37° C. under 0.5 g tension. CCK-8 is added cumulatively to the baths and EC$_{50}$ values in the presence and absence of compounds to be tested are determined, as described in the gall bladder protocol above.

Gastrin Receptor Binding in Guinea Pig Gastric Glands

Guinea pig gastric mucosal glands are prepared by the procedure of Berglingh and Obrink, *Acta Physiol Scand.* 96: 150 (1976), with a slight modification according to Praissman et al. *C. J. Receptor Res.* 3: (1983). Gastric mucosa from male Hartley guinea pigs (300–500 g body weight) are washed thoroughly and minced with fine scissors in standard buffer consisting of the following: 130 mM NaCl, 12 mM NaHCO$_3$, 3 mM NaH$_2$PO$_4$, 3 mM Na$_2$HPO$_4$, 3 mM K$_2$HPO$_4$, 2 mM MgSO$_4$, 1 mM CaCl$_2$, 5 mM glucose, 4 mM L-glutamine and 25 mM HEPES at pH 7.4. The minced tissues are washed and incubated in a 37° C. shaker bath for 40 minutes, with the buffer containing 0.1% collagenase and 0.1% BSA, and bubbled with 95% O$_2$ and 5CO$_2$. The tissues are passed twice through a 5 ml glass syringe to liberate the gastric glands, and then filtered through 200 mesh nylon. The filtered glands are centrifuged at 270 g for 5 minutes and washed twice by resuspension and centrifugation.

The washed guinea pig gastric glands are resuspended in 25 ml of standard buffer containing 0.25 mg/ml of bacitracin. For binding studies, 10 μl of buffer (for total binding) or gastrin (1 μM final concentration, for nonspecific binding) or test compound and 10 μl of $^{125}$I-gastrin (NEN, 2200 Ci/mmole, 25 pM final) or $^3$H-pentagastrin (NEN, 22 Ci/mmole, 1 nM final) are added to 220 μl of gastric glands in triplicate tubes which are aerated with 95% O$_2$ and 5% CO$_2$, and capped. The reaction mixtures, after incubation at 25° C. for 30 minutes, are filtered under reduced pressure on glass G/F B filters (Whatman) and immediately washed with 4×4 ml of standard buffer containing 0.1% BSA. The radioactivity on the filters is measured using a Beckman gamma 5500 for $^{125}$I-gastrin or liquid scintillation counting for $^3$H-pentagastrin.

The ability of the heterocycle-fused benzazepines of the instant invention to antagonize CCK and gastrin makes these compounds useful as pharmaceutical agents for mammals, especially for humans, for the treatment and prevention of disorders wherein CCK and/or gastrin may be involved. Examples of such disease states include gastrointestinal disorders, especially such as irritable bowel syndrome or ulcers, excess pancreatic or gastric secretion, acute pancreatitis, motility disorders or gastrointestinal neoplasms; central nervous system disorders, caused by CCK interactions with dopamine, such as neuroleptic disorders, tardive dyskinesia, Parkinson's disease, psychosis or Gilles de la Tourette Syndrome; disorders of appetite regulatory systems; Zollinger-Ellison syndrome, antral G cell hyperplasia, or pain (potentiation of opiate analgesia); as well as certain tumors of the lower esophagus, stomach, intestines and colon.

The compounds of the instant invention or pharmaceutically-acceptable salts thereof, may be administered to a human subject either alone or, preferably, in combination with pharmaceutically-acceptable carriers, excipients or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to the instant invention, or a salt thereof, is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 mg/kg to about 50 mg/kg of body weight, and preferably, of from 0.1 mg/kg to about 20 mg/kg of body weight, administered in single or divided doses. In some cases, however, it may be necessary to use dosages outside these limits.

In the treatment of irritable bowel syndrome, for instance, 1 to 10 mg/kg of a CCK antagonist might be administered orally (p.o.), divided into two doses per day (b.i.d.). In treating delayed gastric emptying, the dosage range would probably be the same, although the drug might be administered either intravenously (I.V.) or orally, with the I.V. dose probably tending to be slightly lower due to better availability. Acute pancreatitis might be treated preferentially in an I.V. form, whereas spasm and/or reflex esophageal, chronic pancreatitis, past vagatomy diarrhea, or treatment of anorexia or of pain associated with biliary dyskinesia might indicate p.o. form administration.

In the use of a gastrin antagonist as a tumor palliative for gastrointestinal neoplasms with gastrin receptors, as a modulator of central nervous system activity treatment of Zollinger-Ellison syndrome, or in the treatment of peptic ulcer disease, a dosage of 0.1 to 10 mg/kg administered one-to-four times daily might be indicated.

Because these compounds antagonize the function of CCK in animals, they may also be used as feed additives to increase the food intake of animals in daily dosages of about 0.05 to about 50 mg/kg of body weight.

The invention is further defined by reference to the following examples which are intended to be illustrative and not limiting.

EXAMPLE 1

Preparation of 7-phenyl-5H-pyrimido[5,4-d][2]benzazepine (9, $X^1$=H, $R^1$=H, $R^2$=Ph)

This compound is prepared according to the method of Trybrulski et al., *J. Med. Chem.*, 26, 1589-1596 (1983).

EXAMPLE 2

Preparation of 5-oximino-7-phenyl-5H-pyrimido[5,4-d]-[2]benzazepine (44, $X^1$=H, $R^2$=Ph, W=CH, Y=N, Z=CH).

To a suspension of potassium tert-butoxide (24.9 g, 222 mmole) in 600 ml of dry tetrahydrofuran is added 200 ml of dry tert-butylalcohol at $-20°$ C. under nitrogen. To this solution is then added, via addition funnel, 7-phenyl-5H-pyrimido[5,4-d][2]-benzazepine (25 g) in 260 ml of tetrahydrofuran. The resulting solution is stirred for about 2 hours at $-20°$ C. and treated with 17.4 ml (130 mmole) of isoamyl nitrite. The reaction mixture is warmed to 0° C. over approximately 15 minutes and quenched with the addition of 60 ml of cold water and 20 ml of glacial acetic acid. All solvents are removed under reduced pressure and the residue is partitioned between ethyl acetate (600 ml) and brine (100 ml). The phases are separated and the organic extracts are dried ($Na_2SO_4$), concentrated, and triturated with ether.

EXAMPLE 3

Preparation of 5(R,S)-amino-7-phenyl-5H-pyrimido-[5,4-d][2]-benzazepine (45, $X^1$=H, $R^2$=Ph, W=CH, Y=N, Z=CH, n=0)

A solution of 150 ml of methanol containing 5 g of 5-oximino-7-phenyl-5H-pyrimido[5,4-d][2]-benzazepine is treated with a slurry of active Raney-Nickel catalyst[1] in ethanol (10 g). The resulting suspension is hydrogenated on a Parr apparatus at 60 psi and 23° C. for about 30 hours. The catalyst is removed by filtration and the filtrate is concentrated to afford the title compound.
[1] The Raney-nickel catalyst is prepared according to Fieser & Fieser, *Reagents for Organic Synthesis*, Vol. I, John Wiley & Sons, Inc., New York 1967, p. 729.

EXAMPLE 4

Preparation of 5(R,S)-(2(S)-tert-butoxycarbonylamino-3-phenylpropanoylamino)-7-phenyl-5H-pyrimido[5,4-d]-[2]benzazepine Crude 5(R,S)-amino-7-phenyl-5H-pyrimido[5,4-d][2]benzazepine (1.37 g), Boc-L-phenylalanine (1.37 g, 5.17 mmole), 1-hydroxybenzotriazole (HBT) (0.70 g, 5.17 mmole), and 1-ethyl-3-(3-dimethylaminopropyl)-carbodiimide hydrochloride (EDC) (0.99 g, 5.17 mmole) are combined in DMF (30 ml) and stirred at room temperature. The pH of the mixture is adjusted to 9.5 with triethylamine. After about ½ hour, the DMF is removed in vacuo and the residue is partitioned between methylene chloride and 10% citric acid solution. The layers are separated and the organic phase is washed with saturated $NaHCO_3$ solution, water and brine, then dried over $Na_2SO_4$, filtered, and evaporated to dryness in vacuo. The residue is chromatographed on silica gel and the combined product fractions evaporated to dryness in vacuo to give the title compound as a mixture of diastereomers.

EXAMPLE 5

Preparation of 5(R and S)-(2(S)-amino-3-phenyl-propanoylamino)-7-phenyl 5H-pyrimido[5,4-d][2]benzazepine 5(R,S)-(2(S)-tert-Butoxycarbonylamino-3-phenyl-propanolamine)-7-phenyl-5H-pyrimido[5,4-d][2]-benzazepine (1,8 gm) is dissolved in EtOAc (25 ml), cooled to 0° C., and the solution saturated with HCl (g) over a 10 minute period. After stirring an additional 10 minutes, the solvent is removed in vacuo. The product is dissolved in $H_2O$, basified with saturated $Na_2CO_3$ (aqueous) and extracted with EtOAc (3×). The organic layers are combined, washed with brine, dried over $Na_2SO_4$, filtered and rotoevaporated in vacuo. Flash chromatography on silica gel separates the 1/1 pair of diastereomers, with the fractions containing the individual components being concentrated to dryness to give the separated diastereomers.

EXAMPLE 6

Preparation of 5(R)- and 5(S)-amino-7-phenyl-5H-pyrimido[5,4-d][2]-benzazepine

5(S)-(2(S)-amino-3-phenylpropanoylamino)-7-phenyl-5H-pyrimido[5,4-d][2]-benzazepine (1.15 g) is combined with phenylisothiocyanate (395 mg, 2.93 mmole) in $CH_2Cl_2$ (20 ml) and the mixture concentrated on a steam bath. The resulting oil is twice diluted with $CH_2Cl_2$ (20 ml) and both times reconcentrated on the steam bath. The oil is evaporated in vacuo to a foam which is treated with TFA (15 ml) and warmed for 18 minutes in an oil bath thermostatted at 52°. The TFA is removed in vacuo. The residue is treated twice with $CH_2Cl_2$ and with $Et_2O$, evaporated in vacuo after each treatment, and the resulting oil chromatographed on silica gel. The product fractions are evaporated in vacuo, and the residue is dissolved in $CH_2Cl_2$, washed with a small volume of 5% NaOH, dried over $Na_2SO_4$, filtered, and evaporated to give the 5(S)-isomer of the title structure.

5(R)-(2(S)-Amino-3-phenylpropanoylamino)-7-phenyl-5H-pyrimido[5,4-d][2]-benzazepine was converted by the same procedure to the 5(R)-enantiomer of the title compound.

EXAMPLE 7

Preparation of 5(S)-5-(2-indolecarbonylamino)-7-phenyl-5H-pyrimido[5,4 d][2]-benzazepine (48, $X^1$=H, $R^2$=Ph, $R^3$=NHCO-2-indole, W=CH, Y=N, Z=CH).

5(S)-5-Amino-7-phenyl-5H-pyrimido[5,4-d][2]-benzazepine (595 mg) is dissolved in $CH_2Cl_2$ (15 ml) and treated with 2-indolecarbonyl chloride (403 mg, 2.24 mmole) followed by triethylamine (227 mg, 2.24 mmole). The mixture is stirred at room temperature for about 30 minutes and concentrated in vacuo with the residue being chromatographed on silica gel and the combined product fractions evaporated to dryness in vacuo. Three times, $Et_2O$ (15 ml) is added and evaporated in vacuo to give the title compound.

EXAMPLE 8

Preparation of 5(R)-5(3-methoxyphenylaminocarbonylamino)-7-phenyl-5H-pyrimido[5,4-d][2]-benzazepine (47, $X^1$=H, $R^2$-Ph,

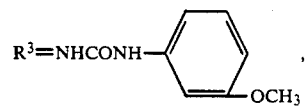

W=CH, Y=N, Z=CH)

To a solution of 85 mg of 5(R)-amino-7-phenyl-5-pyrimido[5,4-d][2]benzazepine in 8 ml of dry tetrahydrofuran is added 3-methoxyphenylisocyanate (40 μl, 0.315 mmole) at room temperature. The mixture is stirred for about 8 hours, at which time the reaction mixture is filtered, and the collected solids washed with hot methanol and dried in vacuo to give the title product.

EXAMPLE 9

Preparation of 2-methyl-6-phenyl-4H-triazolo[5,4-d]-[2]benzazepine (18, X=H, $R^1$—$CH_3$, $R^2$=phenyl)

This compound is prepared according to the method of Benjamin, et al., *J. Med. Chem.*, 26, 100–103 (1983).

EXAMPLE 10

Preparation of 2-methyl-4-oximino-6-phenyl-4H-thiazolo[5,4-d][2]benzazepine (44, $X^1$=H, $R^2$=Ph, W=C—$CH_3$, Y=S, Z is absent)

This compound is prepared according to the method of Example 2.

EXAMPLE 11

4-Amino-2-methyl-6-phenyl-4H-thiazolo[5,4-d][2]benzazepine (45, $X^1$=H, $R^2$=Ph, W=C—$CH_3$, Y=S, Z is absent)

This compound is prepared according to the method of Example 3 and resolved according to the methods of Examples 4–6.

EXAMPLE 12

4(S)-4-(4-Chlorophenylcarbonylamino)-2-methyl-6-phenyl-4H-thiazolo[5,4-d][2]benzazepine (48, $X^1$=H, $R^2$=Ph,

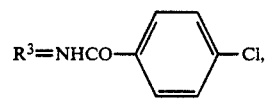

W=C—$CH_3$, Z=S, Z is absent)

This compound is prepared according to the method of Example 7.

EXAMPLE 13

4(R)-4-(3-Methylphenylaminocarbonylamino)-2-methyl-6-phenyl-4H-thiazolo[5,4-d][2]benzazepine (47, $X^1$=H, $R^2$=Ph,

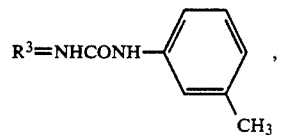

W=C—$CH_3$, Y=S, Z is absent)

This compound is prepared according to the method of Example 8.

EXAMPLE 14

6-Phenyl-4H-oxazolo[5,4-d][2]benzazepine (30, X¹=H, R²=Ph, R¹=H, W=CH, Y=O, Z is absent)

This compound is prepared according to the methods of Trybulski et al., *J. Med. Chem.*, 26, 1596-1601 (1983).

EXAMPLE 15

4-Oximino-6-phenyl-4H-oxazolo[5,4-d][2]benzazepine (44, X¹=H, R²=Ph, W=CH, Y=O, Z is absent)

This compound is prepared according to the methods of Example 2.

EXAMPLE 16

4-Amino-6-phenyl-4H-oxazolo[5,4-d][2]benzazepine (45, X¹=H, R²=Ph, W=CH, Y=O, Z is absent, n=0)

This compound is prepared according to the methods of Example 3 and resolved according to the methods of Examples 4 through 6.

EXAMPLE 17

4-(S)-4-(2-Indolecarbonylamino)-6-phenyl-4H-oxazolo-[5,4-d]-[2]-benzazepine (48, X¹=H, R²=Ph, R³=NHCO-2-indole, W=CH, Y=O, Z is absent)

This compound is prepared according to the method of Example 7.

EXAMPLE 18

4(R)-4-(3-Chlorophenylaminocarbonylamino)-6-phenyl-4H-oxazolo[5,4-d]-[2]-benzezapine (47, X¹=H, R²=Ph,

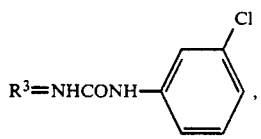

W=CH, Y=O, Z is absent)

This compound is prepared according to the method of Example 8.

EXAMPLE 19

6-Phenyl-2H,4H-[1,2,3]triazolo[4,5-d][2]benzazepine (34, X¹=H, R²=Ph)

This compound is prepared according to the methods of Trybulski, et al., *J. Med. Chem.*, 26, 367-372 (1983).

EXAMPLE 20

4-Oximino-6-phenyl-2H,4H-[1,2,3]triazolo[4,5-d][2]-benzazepine (44, X¹=H, R²=Ph, W=NH, Y=N, Z is absent)

This compound is prepared according to the method of Example 2.

EXAMPLE 21

4-Amino-6-phenyl-2H,4H-[1,2,3]triazolo[5,4-d][2]-benzazepine (45, X¹=H, R²=Ph, W=NH, Y=N, Z is absent)

This compound is prepared according to the method of Example 3 and resolved according to the methods of Examples 4 through 6.

EXAMPLE 22

4(R)-4-(3-Methoxyphenylaminocarbonylamino)-6-phenyl-2H,4H[1,2,3]triazolo[5,4-d][2]benzazepine (47, X¹=H, R²=Ph,

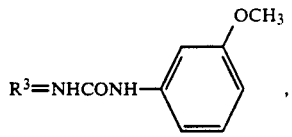

W=NH, Y=N, Z is absent)

This compound is prepared according to the method of Example 8.

EXAMPLE 23

4-(S)-4-(2-Indolecarbonylamino)-6-phenyl-2H,4H-[1,2,3]benzazepine (48, X¹=H, R²=Ph, R³=NHCO-2-indole, W=NH, Y=N, Z is absent)

This compound is prepared according to the method of Example 7.

What is claimed is:

1. A 2-benzazepine of the formula:

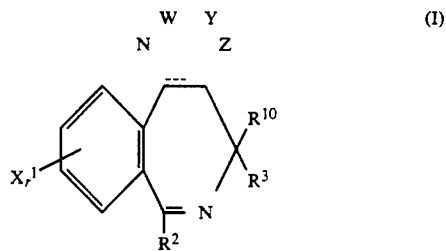

(I)

$R^1$ is H, $C_1$-$C_4$-alkyl, cyclo-$C_3$-$C_7$-alkyl,

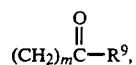

$NR^4R^5$, $C_1$-$C_4$-alkoxy, thio-$C_1$-$C_4$-alkoxy, OH, or SH;

$R^2$ is H; $C_1$-$C_4$-alkyl; mono- or disubstituted or unsubstituted phenyl, where the substituent(s) is/are independently selected from the group consisting of halo, $C_1$-$C_4$-alkyl, $C_1$-$C_4$-alkoxy, $C_1$-$C_4$-alkylthio, carboxyl, carboxy-$C_1$-$C_4$-alkyl, nitro, —$CF_3$,

and hydroxy; 2-, 3- or 4-pyridyl; or —$(CH_2)_m COOR^6$;

$R^3$ is —$(CH_2)_n R^7$,

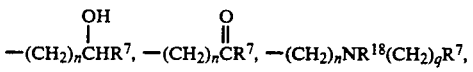

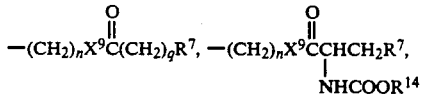

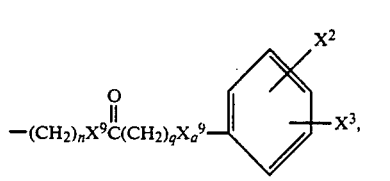

-continued

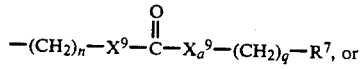

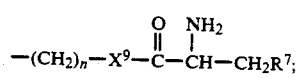

$R^4$ and $R^5$ are independently H, $C_1$-$C_4$-alkyl, or cyclo-$C_3$-$C_7$-alkyl or are connected to form a hetero ring of the structure

wherein k is 2 to 6;

$R^6$ is H, $C_1$-$C_4$-alkyl, cyclo-$C_3$-$C_7$-alkyl, unsubstituted or mono- or disubstituted phenyl, wherein the substituent(s) is/are independently selected from the group consisting of halo, $C_1$-$C_4$-alkyl, $C_1$-$C_4$-alkoxy, nitro, and $CF_3$, or unsubstituted or mono- or disubstituted phenyl-$C_1$-$C_4$-alkyl, wherein the substituent(s) is/are selected from the group consisting of halo, $C_1$-$C_4$-alkyl, $C_1$-$C_4$-alkoxy, nitro, and $CF_3$;

$R^7$ is α- or β-naphthyl, unsubstituted or mono- or disubstituted phenyl, wherein the substituent(s) is/are independently selected from the group consisting of halo, $-NO_2$, $-OH$, $-NR^4R^5$, $C_1$-$C_4$-alkyl, cyano, phenyl, trifluoromethyl, acetylamino, acetyloxy, $C_1$-$C_4$-alkylthio, $SCF_3$, $C\equiv CH$, $CH_2SCF_3$, $OCHF_2$, S-phenyl, and $C_1$-$C_4$-alkoxy,

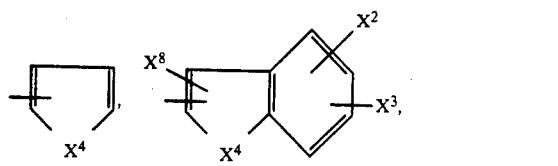

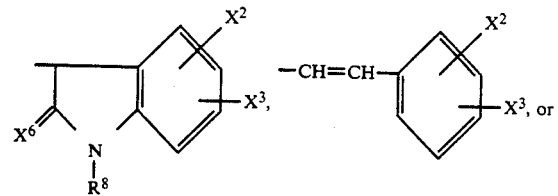

$R^8$ is H, $C_1$-$C_4$-alkyl, cyclo-$C_3$-$C_7$-alkyl, $-(CH_2)_n$-cyclo-$C_3$-$C_7$-alkyl, O $$-C-C_1-C_4\text{-alkyl, or } -COCHNHCOOR^{11};$$
$$\phantom{-C-C_1-C_4\text{-alkyl, or }-COCH}CH_2R^{12}$$

$R^9$ is OH, $OR^{11}$ or

$R^{10}$ is H, $-OH$, or $-CH_3$;
$R^{11}$ and $R^{12}$ are independently $C_1$-$C_4$-alkyl or cyclo-$C_3$-$C_7$-alkyl;

$R^{13}$ is

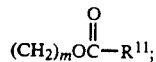

$R^{14}$ is $C_1$-$C_4$-alkyl or phenyl-$C_1$-$C_4$-alkyl;
$R^{18}$ is H, $C_1$-$C_4$-alkyl, formyl, acetyl, propionyl or butyryl;
m is 1 to 4;
n is 0 to 4;
q is 0 to 4:
r is 1 or 2;
$X^1$ is H, $-NO_2$, $CF_3$ CN, OH, $C_1$-$C_4$-alkyl, halo, $C_1$-$C_4$-alkylthio, $C_1$-$C_4$-alkoxy, $-(CH_2)_nCOOR^6$, $-NR^4R^5$, or

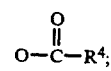

$X^2$ and $X^3$ are independently H, $-OH$, $-NO_2$, halo, $C_1$-$C_4$-alkylthio, $C_1$-$C_4$-alkyl, $C_1$-$C_4$-alkoxy or

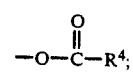

$X^4$ is S, O, $CH_2$, or $NR^8$;
$X^6$ is O or HH;
$X^8$ is H or $C_1$-$C_4$-alkyl;
$X^9$ and $X_a^9$ are independently $NR^{18}$ or O;
W is $CR^1$, N or NH;
Y is N, S, or O;
Z is C—H or absent; and
$\underline{\phantom{---}}$ is a saturated (single) or unsaturated (double) bond;
or a pharmaceutically-acceptable salt thereof.

2. A 2-benzazepine according to claim 1, wherein
$R^1$ is H or $C_1$-$C_4$-alkyl;
$R^2$ is unsubstituted of mono- or disubstituted phenyl where the substitutent(s) is/are selected from the group consisting of halo, $C_1$-$C_4$-alkyl, $C_1$-$C_4$-alkoxy, nitro, and $-CF_3$;
$R^3$ is $-(CH_2)_nR^7$,

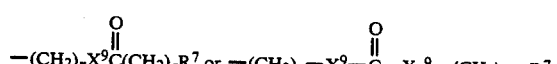

$R^7$ is α- or β-naphthyl, unsubstituted or mono- or disubstituted phenyl, where the substituent(s) is/are selected from the group consisting of halo, nitro, $C_1$-$C_4$-alkyl, trifluoromethyl and $C_1$-$C_4$-alkoxy,

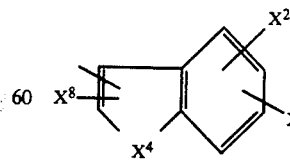

$R^8$ is H, or $C_1$-$C_4$-alkyl;
n is 0 -to- 2;
q is 0 -to- 2;
r is 1 or 2;
$X^1$ is H, $-NO_2$, $C_1$-$C_4$-alkyl, halo, or $C_1$-$C_4$-alkoxy;

$X^2$ and $X^3$ are independently H, —$NO_2$, halo, $C_1$-$C_4$-alkyl or $C_1$-$C_4$-alkoxy;
$X^4$ is S, O, $CH_2$, or $NR^8$;
$X^8$ is is H or $C_1$-$C_4$-alkyl;
$X^9$ and $X_a^9$ are independently NH or O; and or a pharmaceutically-acceptable salt thereof.

3. A 2-benzazepine according to claim 1, wherein
$R^1$ is H or methyl;
$R^2$ is phenyl or o-F-phenyl;
$R^3$ is

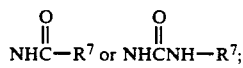

$R^7$ is

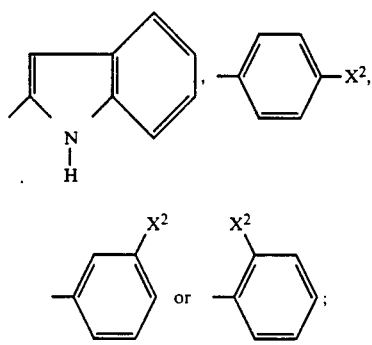

$X^1$ is H;
$X^2$ is H, —$NO_2$, halo, methyl, or methoxy;
W is $CR^1$;
Y is N; and
Z is CH.

4. A 2-benzazepine according to claim 1, wherein
$R^1$ is H or methyl;
$R^2$ is phenyl or o-F-phenyl;
$R^3$ is

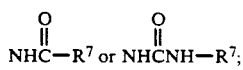

$R^7$ is

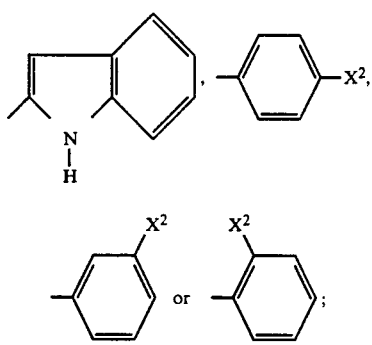

$X^1$ is H;
$X^2$ is H, —$NO_2$, halo, methyl, or methoxy;
W is $CR^1$;
Y is S; and
Z is absent.

5. A 2-benzazepine according to claim 1, wherein
$R^1$ is H or methyl;
$R^2$ is phenyl o-F-phenyl;
$R^3$ is

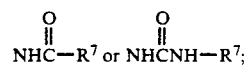

$R^7$ is

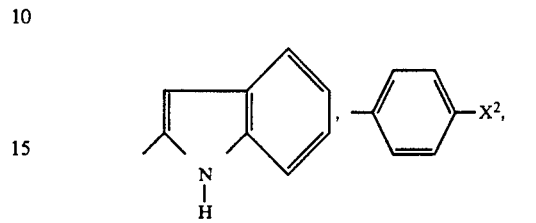

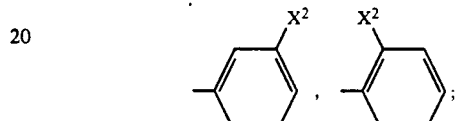

$X^1$ is H;
$X^2$ is H, —$NO_2$, halo, methyl, or methoxy;
W is $CR^1$;
Y is 0; and
Z is absent.

6. A 2-benzazepine according to claim 1, wherein
$R^2$ is phenyl or o-F-phenyl;
$R^3$ is

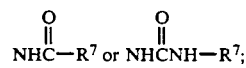

$R^7$ is

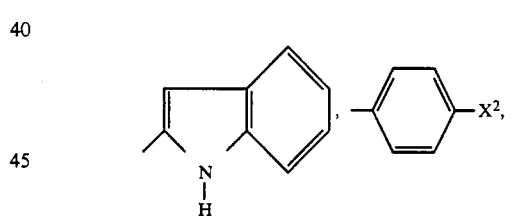

$X^1$ is H;
$X^2$ is H, —$NO_2$, halo, methyl, or methoxy;
W is NH;
Y is N; and
Z is absent.

7. A 2-benzazepine according to claim 1 which is:
5(S)-5-(2-indolecarbonylamino)-7-phenyl-5H-pyrimido-[5,4-d][2]benzazepine;
4(S)-4-(4-chlorophenylcarbonylamino)-2-methyl-6-phenyl-4H-thiazolo-[5,4-d][2]benzazepine;
4(S)-4-(2-indolecarbonylamino)-6-phenyl-4H-oxazolo-[5,4-d][2]benzazepine; or
4(S)-4-(2-indolecarbonylamino)-6-phenyl-2H,4H-[1,2,3]-triazolo-[5,4-d][2]benzazepine.

8. A 2-benzazepine according to claim 1, which is:
5(R)-5-(3-methoxyphenylaminocarbonylamino)-7-phenyl-5H-pyrimido[5,4-d][2]benzazepine;
4(R)-4-(3-methylphenylaminocarbonylamino)-2-methyl-6-phenyl-4H-[5,4-d][2]benzazepine;
4(R)-4-(3-chlorophenylaminocarbonylamino)-6-phenyl-4H-oxazolo-[5,4-d][2]benzazepine; or
4(R)-4-(3-methoxyphenylaminocarbonylamino)-6-phenyl-2H, 4H-[1,2,3]triazolo-[5,4-d][2]benzazepine;

9. A composition comprising a therapeutically-effective amount for antagonism of the function of cholecystokinins or gastrin in mammals of one or more 2-benzazepines according to claim 1, or pharmaceutically-acceptable salts thereof, and a pharmaceutically-acceptable carrier.

10. A composition according to claim 9, further comprising an adjuvant.

11. A composition according to claim 9, wherein the therapeutically-effective amount is about 0.05 to 50 mg/kg of body weight.

12. A composition according to claim 9, wherein the mammals are humans.

13. A method of preventing in mammals or treating mammals for disorders of the gastrointestinal, central nervous or appetite regulatory systems which comprises administering to those mammals a therapeutically-effective amount of one or more 2-benzazepines, or therapeutically-acceptable salts thereof, according to claim 1.

14. A method according to claim 13, wherein a pharmaceutically-acceptable carrier or a pharmaceutically-acceptable carrier and an adjuvant are also administered.

15. A method according to claim 13, wherein a therapeutically-effective amount is from about 0.1 to about 20 mg/kg of body weight, administered in single or divided doses.

16. A method of increasing food intake in animals which comprises administering as a food additive between about 0.05 mg/kg and about 50 mg/kg of body weight of one or more compounds or pharmaceutically-acceptable salts according to claim 1.

* * * * *